United States Patent
Mach et al.

(10) Patent No.: US 9,593,361 B2
(45) Date of Patent: Mar. 14, 2017

(54) SALMONELLA DETECTION ARTICLES AND METHODS OF USE

(75) Inventors: Patrick A. Mach, Shorewood, MN (US); Mara S. Reif-Wenner, Red Wing, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/118,258

(22) PCT Filed: May 14, 2012

(86) PCT No.: PCT/US2012/037701
§ 371 (c)(1),
(2), (4) Date: Nov. 18, 2013

(87) PCT Pub. No.: WO2012/161992
PCT Pub. Date: Nov. 29, 2012

(65) Prior Publication Data
US 2014/0087406 A1     Mar. 27, 2014

Related U.S. Application Data

(60) Provisional application No. 61/488,492, filed on May 20, 2011.

(51) Int. Cl.
| | | |
|---|---|---|
| A61K 38/00 | (2006.01) | |
| G01N 33/569 | (2006.01) | |
| C12Q 1/34 | (2006.01) | |
| C12Q 1/04 | (2006.01) | |
| C12Q 1/10 | (2006.01) | |
| C12M 1/12 | (2006.01) | |
| C12M 1/34 | (2006.01) | |

(52) U.S. Cl.
CPC .............. *C12Q 1/34* (2013.01); *C12M 25/06* (2013.01); *C12M 41/36* (2013.01); *C12Q 1/045* (2013.01); *C12Q 1/10* (2013.01)

(58) Field of Classification Search
CPC .............................. G01N 33/569; A61K 38/00
See application file for complete search history.

(56) References Cited

U.S. PATENT DOCUMENTS

| | | | | |
|---|---|---|---|---|
| 4,279,995 A | * | 7/1981 | Woods ..................... | C12Q 1/10 435/38 |
| 4,565,783 A | * | 1/1986 | Hansen ..................... | C12Q 1/04 435/30 |
| 5,409,838 A | | 4/1995 | Wickert | |
| 5,786,167 A | | 7/1998 | Tuompo et al. | |
| 6,022,682 A | | 2/2000 | Mach et al. | |
| 7,150,977 B2 | | 12/2006 | Restaino | |
| 9,029,118 B1 | | 5/2015 | Olstein | |
| 2004/0029212 A1 | | 2/2004 | Rodriguez Martinez et al. | |
| 2005/0196825 A1 | * | 9/2005 | Roth ........................ | C12Q 1/04 435/34 |

FOREIGN PATENT DOCUMENTS

| | | |
|---|---|---|
| EP | 2 455 447 | 5/2012 |
| JP | H9-511917 | 12/1997 |
| JP | 2004-57054 | 2/2004 |
| JP | 2008-536492 | 9/2008 |
| JP | 2011-502546 | 1/2011 |
| WO | WO 94/28163 | 12/1994 |
| WO | WO 96/30543 | 10/1996 |
| WO | WO 97/36001 | 10/1997 |
| WO | WO 02/00921 | 1/2002 |
| WO | WO 02/20829 | 3/2002 |
| WO | WO 2004/111263 | 12/2004 |
| WO | WO 2006/107583 | 10/2006 |
| WO | WO 2009/108229 | 9/2009 |
| WO | WO 2010/077619 | 7/2010 |
| WO | WO 2010/147918 | 12/2010 |
| WO | WO 2012/092181 | 7/2012 |

OTHER PUBLICATIONS

Wondwossen et al. (Antimicrobial Resistance of *Salmonella* Isolates from Swine. Journal of Clinical Microbiology 2000 38(12): 4633-4636).*
Manafi, M.; "New developments in chromogenic and fluorogenic culture media"; International Journal of Food Microbiology; vol. 60; 2000; pp. 205-218 (XP-002177549).
Antibiotics (1975), vol. 20, No. 10, pp. 911-917.
Tanabe, M. et al.; An Epidemic of Multiresistant *Salmonella typhimurium* with a Characteristic Plasmid Profile among Calves in Tokachi District, Japan; Jpn. J. Vet. Sci;; 1988; vol. 50, No. 5; pp. 1025-1034.
Brochure from BD entitled "BBL™ Urea Agar Base Concentrate 10X; BBL™ Urea Agar Slants, Complete—Quality Control Procedures"; 2015; 3 pgs.
Christensen, W.; "Urea Decomposition as a Means of Differentiating Proteus and Paracolon Cultures from Each Other and from *Salmonella* and Shigella Types"; J. Bacteriol; vol. 52; 1946; pp. 461-466.
Gorke, B. et al.; "Carbon catabolite repression in bacteria: many ways to make the most out of nutrients"; Nature Reviews Microbiology; vol. 6; 2008; pp. 613-624 Abstract Only.

* cited by examiner

*Primary Examiner* — Scott Long
*Assistant Examiner* — Natalie Moss

(57) ABSTRACT

An article for detecting *Salmonella* microorganisms is provided. The article comprises a highly selective nutrient medium and a plurality of indicator systems. A method of using the article to detect *Salmonella* microorganisms is also provided.

5 Claims, 1 Drawing Sheet

SALMONELLA DETECTION ARTICLES AND METHODS OF USE

CROSS REFERENCE TO RELATED APPLICATIONS

This application is a national stage filing under 35 U.S.C. 371 of PCT/US2012/037701, filed May 14, 2012, which claims priority to U.S. Provisional Patent Application No. 61/488,492, filed May 20, 2011, the disclosure of which is incorporated by reference in its entirety herein.

BACKGROUND

*Salmonella* microorganisms are a significant causative agent of food-borne illness. These microorganisms can be found in uncooked meats, vegetables, dairy and processed foods, such as peanut butter. A *Salmonella* infection can results in symptoms of enterocolitis such as fever, abdominal pain and diarrhea, as well as occasion nausea and vomiting. Large food manufacturing facilities are sources of contaminated food products that may be distributed to large numbers of consumers, many of who can become infected with the bacteria.

SUMMARY

In general, the invention relates to an article, a system, and a method for detecting a microorganism. In particular, the system and method can be used to detect microorganisms belonging to the genus *Salmonella*. The inventive article includes a nutrient medium and a highly selective combination of agents that substantially prevent the growth of most microorganisms, while permitting the growth of *Salmonella* microorganisms. The article further includes up to three indicator systems, each indicator system serving a unique function to indicate the possible presence of a *Salmonella* microorganism. When the inventive article indicates the possible presence of a *Salmonella* microorganism, a fourth unique indicator system can be used further to indicate the presence of a *Salmonella* microorganism. Advantageously, the system and method can be used to indicate the presence of a *Salmonella* microorganism within several hours after the method is initiated.

In one aspect, the present disclosure provides a culture device for detecting a target microorganism. The culture device can comprise a selective growth medium that includes nutrients to facilitate the growth of the target microorganism and a plurality of selective agents that includes Cefsulodin, Nalidixic Acid, Streptomycin, Methicillin, and bile salts. The culture device further can comprise a first differential indicator system and a gelling agent.

In any embodiment, the culture device further can comprise a nondifferential indicator system to indicate the presence of the target microorganism. In any of the above embodiments, the first differential indicator system can comprise a pH indicator. In any of the above embodiments, the culture device further can comprise a second differential indicator system to indicate the presence of a nontarget microorganism. In any of the above embodiments, the second differential indicator can comprise a chromogenic β-galactosidase enzyme substrate. In any of the above embodiments, the selective growth medium can comprise a dry, rehydratable selective growth medium, wherein the gelling agent comprises a dry, cold water-soluble gelling agent. In any of the above embodiments, the culture device can be a thin film culture device.

In yet another aspect, the present disclosure provides a method of detecting a *Salmonella* microorganism. The method can comprise providing a liquid sample, any of the above culture devices, and a third differential indicator system. The method further can comprise contacting a predefined volume of the sample, in the culture device, with the selective growth medium; the first indicator system; the nondifferential indicator system, if present; the second indicator system, if present; and the gelling agent to form an inoculated culture device. The method further can comprise incubating the inoculated culture device for a first period of time; observing the growth medium to detect an indication of a possible presence in the sample of the target microorganism; when there is an indication of the possible presence of the target microorganism, contacting the third differential with the hydrated growth medium; and observing the third differential indicator system in the hydrated growth medium for an indication of the presence of the target microorganism.

In yet another aspect, the present disclosure provides a method of detecting *Salmonella* microorganisms. The method can comprise providing a sample, any of the above thin film culture devices, and a third differential indicator system. The method further can comprise, in the culture device, contacting a predefined volume of a *Salmonella*-free aqueous liquid with the selective growth medium; the first differential indicator system; the nondifferential indicator system, if present; the second differential indicator system, if present; and the gelling agent to form a hydrated growth medium. The method further can comprise inoculating the hydrated growth medium with the sample to form an inoculated culture device; incubating the inoculated culture device for a first period of time; observing the hydrated growth medium to detect an indication of a possible presence in the sample of the target microorganism; when there is an indication of the possible presence of the target microorganism, contacting the third differential with the hydrated growth medium; and observing the third differential indicator system in the hydrated growth medium for an indication of the presence of the target microorganism.

In any of the above embodiments of the method, detecting an indication of the possible presence of the target microorganism further can comprise observing a colony that reacts with the nondifferential indicator system and the first differential indicator system but does not react with the second differential indicator system. In any of the above embodiments, after contacting the second component with the hydrated growth medium, the method further can comprise incubating the culture device for a second period of time. In any of the above embodiments of the method, incubating the inoculated culture device for a first period of time can comprise incubating the inoculated culture device for about 0.5 hours to about 24 hours. In any of the above embodiments of the method, incubating the inoculated culture device for a second period of time can comprise incubating the inoculated culture device for about 30 minutes to about 360 minutes.

In another aspect, the present disclosure provides a system for detecting a *Salmonella* microorganism. The system can comprise a culture device comprising a nutrient medium that is highly selective for *Salmonella* microorganisms and at least two differential indicator systems, wherein a first differential indicator system is a positive indicator of the *Salmonella* microorganism and a second differential indicator system is a negative indicator of the *Salmonella* microorganism. The system further can comprise a detection article comprising a third differential indicator system, wherein the third differential indicator system is a positive indicator of the *Salmonella* microorganism.

In any embodiment of the system, each of the second and third differential indicator systems can comprise a chromogenic enzyme substrate, wherein each chromogenic enzyme substrate comprises a carbohydrate component and a chromophore. In any embodiment of the system, each of the second and third differential indicator systems can comprise the same chromophore. In any embodiment of the system, the second differential indicator system can comprise a chromogenic indicator of β-galactosidase enzyme activity. In any embodiment of the system, the third differential indicator system comprises a chromogenic indicator of α-galactosidase enzyme activity.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The term "nondifferential indicator system", as used herein, refers to a general indicator system such as an indicator dye, for example, that does not distinguish different types of microorganisms.

The term "differential indicator system", as used herein, refers to an indicator system that distinguishes between two or more types of microorganisms. In some embodiments, a differential indicator system may comprise, for example, a carbohydrate and a pH indicator wherein the system can distinguish between microorganisms that ferment the carbohydrate to acid end products and microorganisms that don't ferment the carbohydrate to acid end products. In some embodiments, a differential indicator system can comprise a chromogenic or fluorogenic enzyme substrate wherein the system can distinguish between microorganisms that comprise an enzyme to react with the enzyme substrate and microorganisms that don't comprise an enzyme to react with the enzyme substrate.

The terms "comprises" and variations thereof do not have a limiting meaning where these terms appear in the description and claims.

As used herein, "a," "an," "the," "at least one," and "one or more" are used interchangeably. Thus, for example, a microorganism can be interpreted to mean "one or more" microorganisms.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

DETAILED DESCRIPTION

Current methods to detect *Salmonella* microorganisms in food samples include the use of a selective enrichment procedure to increase the number and/or concentration of target (*Salmonella*) microorganisms, relative to the nontarget microorganisms (e.g., non-*Salmonella* Enterobacteriaceae: *Citrobacter, E. coli, Proteus/Morganella/Providencia*, non-Enterobactericeae: *Aeromonas*, etc. After the enrichment procedure, which typically lasts 16-48 hours, the resulting culture can be tested for the presence of *Salmonella* microorganisms by a variety of techniques that are known in the art such as, for example, plating techniques, immunodiagnostic techniques (e.g., ELISA, immunochromatography), and genetic techniques (e.g., PCR, rt-PCR, hybridization techniques). Each of the techniques requires additional time to identify the *Salmonella* microorganisms, require highly-trained operators to perform the techniques and/or interpret the results, and often require costly reagents, devices, and or equipment.

Figure 1:
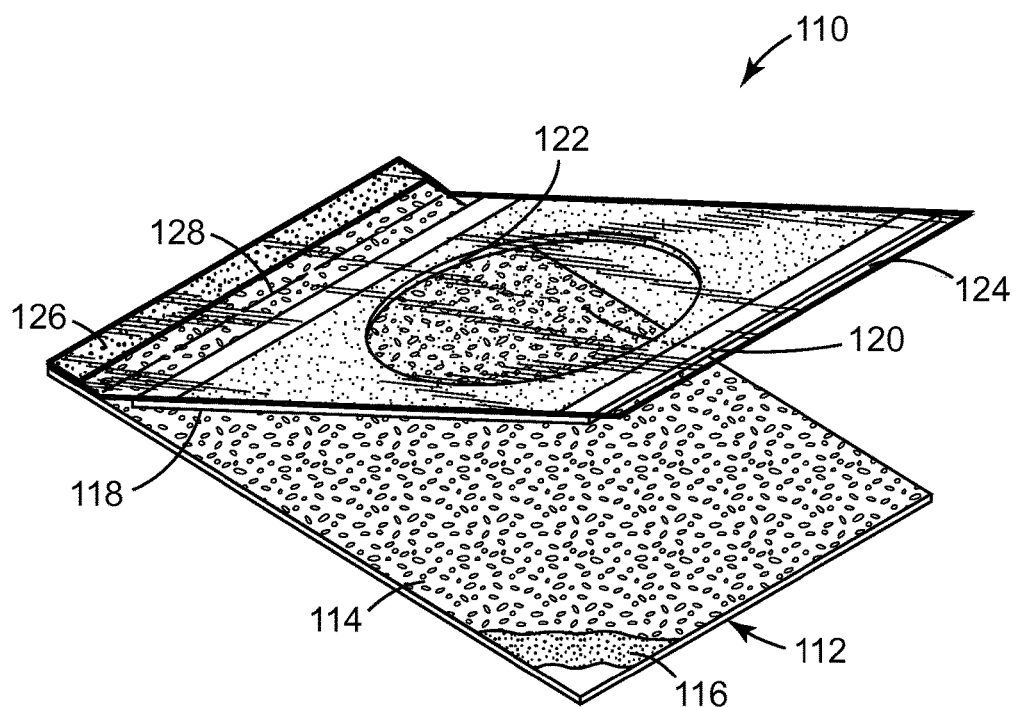
FIG. 1 is a top perspective view of one embodiment of a culture device to detect *Salmonella* microorganisms according to the present disclosure.

The present disclosure provides a culture device for detecting *Salmonella* microorganisms. FIG. 1 shows a top perspective view of one embodiment of a partially-open culture device 110 according to the present disclosure. The culture device 110 is similar in construction to the dry film culture devices disclosed in U.S. Pat. No. 4,565,783, which is incorporated herein by reference in its entirety.

The culture device 110 comprises a self-supporting waterproof substrate 112 and a cover sheet 124. In a closed position, the cover sheet 124 lies adjacent the substrate 112.

Substrate 112 is preferably a relatively stiff film of a material such as polyester, polypropylene or polystyrene which will not absorb or otherwise be affected by water. Polyester films approximately 0.004 to 0.007 inch thick, polypropylene films approximately 0.004 to 0.008 inch thick and polystyrene films approximately 0.015 inch thick have been found to work well. Other suitable substrates include paper with a polyethylene or other water-proof coating. The substrate 12 may be either transparent or opaque, depending on whether one wishes to view bacterial colonies through the substrate. To facilitate the counting of bacterial colonies, the substrate 12 preferably has a square grid pattern printed thereon.

Substrate 12 is coated on its upper surface with a layer of an adhesive 116 which serves to hold the powder 114, which comprises a dry gelling agent and/or nutrients in a uniform monolayer for easy hydration. Adhesive 116 must be water-insoluble and non-inhibitory to the growth of microorganisms. Preferably, the adhesive 116 is sufficiently transparent when wet to enable the viewing of bacterial colonies through the film coated with the adhesive 116. It is preferred that adhesive 116 be pressure-sensitive. However, heat-activated adhesives wherein a lower melting substance is coated onto a higher melting substance may also be used.

Water-activated adhesives such as mucilage may also be useful. Adhesive 116 should be coated onto substrate 112 in a thickness which is preferably less than the diameter of the particles of the powdered gelling agent and/or nutrients. The object is to apply enough adhesive 116 to adhere the particles to the substrate but not so much that the particles become completely embedded in the adhesive 116.

A uniform monolayer of powder 114 is desired with sufficient surface area exposed for hydration. Generally, an adhesive layer in the thickness range of 0.0002 to 0.0005 inch is suitable. A preferred adhesive 116 is a copolymer of isooctylacrylate/acrylamide (in a mole ratio of 94/6). Other pressure sensitive adhesives which may be used include isooctylacrylate/acrylic acid (in a mole ratio of 95/5 or 94/6) and silicone rubber. Adhesives which turn milky upon exposure to water are less preferred, but may be used in conjunction with a non-transparent substrate or where colony visualization is not required.

A monolayer of cold-water-soluble powder 114 is adhered uniformly to adhesive layer 116. Powder 114 comprises at least one ingredient selected from the group consisting of a gelling agent, one or more nutrients for growing microorganisms, and a mixture of a gelling agent and one or more nutrients for growing microorganisms. As used in the specification and claims, the term "powder" designates a finely divided particulate material having an average diameter of less than 400 micrometers. As used in the specification and claims, the term "cold-water-soluble" designates material which forms a solution in water at room temperature.

The "cold-water-solubility" of the powders employed in the devices of the present invention may result, for example, from the inclusion in these powders of an appropriate gelling agent. Suitable gelling agents for inclusion in powder 114 include both natural and synthetic gelling agents which form solutions in water at room temperature. Gelling agents such as hydroxyethyl cellulose, carboxymethyl cellulose, polyacrylamide, locust bean gum and algin form solutions in water at room temperature and are suitable gelling agents for providing powders which are "cold-water-soluble".

As indicated, powder 114 may comprise only a gelling agent. Where the device, as manufactured, contains a powder comprising only gelling agent, the end user adds his own special nutrients "tailored" to the type of microorganisms he wishes to grow. For example, dry powdered nutrients may be suspended in a rapidly-evaporating liquid such as ethanol or "Freon". In other instances, dry powdered nutrients may be suspended or dissolved in aqueous solutions. An aliquot of the liquid is added to the surface of substrate 112 which has been coated previously with adhesive and gelling agent. The liquid is allowed to evaporate, leaving ample nutrients along with the gelling agent.

Where gelling agent is included in powder 114, a sufficient amount of the gelling agent is adhered to the substrate 112 so that a predetermined quantity of water or an aqueous sample, e.g., 1-3 milliliters, placed on the substrate will form a gel having a viscosity of about 1500 cps or more when measured at 60 rpm with a Brookfield Model L VF viscometer at 25° C. Gels of this viscosity will allow convenient handling and stacking and provide distinct colony identification. In most cases 0.025 to 0.050 gram of guar gum on a surface area of 3.14 sq. inches will provide a sufficiently viscous gel when hydrated with 1-3 milliliters of an aqueous sample. The size of the powder particles can be used to control the coating weight per unit area. For example, approximately 100 mesh guar gum coats to a weight of about 0.05 grams/2 inch diameter disc; and a 400 mesh guar gum coats to a weight of about 0.025 grams/2 inch diameter disc. If additional amounts of gelling agent and/or nutrients are required, the cover sheet 124 of this embodiment may also be coated, as described herein.

In any embodiment, culture devices of the present disclosure can comprise a nondifferential indicator such as triphenyltetrazolium chloride (TTC), for example. In some embodiments, it may be desirable to incorporate a nondifferential indicator system into the powder 114. Alternatively, the nondifferential indicator system (e.g., a dye) may be incorporated in the adhesive 116. Suitable dyes are those which are metabolized by any growing microorganism, and which cause the colonies to be colored for easier visualization. Examples of such dyes include triphenyl tetrazolium chloride (TTC), p-tolyl tetrazolium red, tetrazolium violet, veratryl tetrazolium blue and related dyes.

For some uses it may be desirable to form a medium stiff enough to allow inoculation of microorganisms by streaking. To form streakable medium, it may be desirable to include a small amount of cross-linking agent in powder 114 where powder 114 includes a gelling agent. For example, with guar gum, cross-linking agents such as potassium tetraborate, aluminum or calcium salts may be added in an amount less than 1.0 percent by weight of powder 114. One must be careful to select a cross-linking agent which does not substantially affect the growth of the intended microorganism.

Cover sheet 124 is preferably transparent to facilitate visualization and, optionally, counting of the bacterial colonies and is substantially impermeable to bacteria and water vapor. As used in the specification and claims, "substantially impermeable to bacteria and moisture vapor" designates cover sheets which prevent undesired contamination of the dehydrated medium during shipping, storage and use of the devices and which provide an environment which will support the growth of microorganisms during the incubation period. Generally, the cover sheet 124 will have the same properties as substrate 112, but need not be as stiff. A preferred material for cover sheet 124 is a 1.6 mil biaxially-oriented polypropylene film. Cover sheet 124, may be coated with an optional layer of adhesive (not shown). In certain preferred embodiments, cover sheet 124 may be adhered to substrate 112 via a double-sided adhesive tape 126 or a pressure-sensitive adhesive only, for example.

Coated on at least a portion of a surface of the cover sheet 124 is a coating 120 which is substantially water-free and which consists essentially of a cold-water-reconstitutable material comprising a component selected from the group consisting of a gelling agent, one or more selective agents, one or more nutrients for growing microorganisms, a non-differential indicator system, one or more differential indicator systems, and a combination of any two or more of the foregoing components. As used in the specification and claims, the phrase "substantially water-free" designates a coating which has a water content no greater than about the water content of the dehydrated coating once it has been permitted to equilibrate with the ambient environment.

The material employed in the coating 120 is cold-water-reconstitutable. As used in the specification and claims, "cold-water-reconstitutable" designates material which forms a solution, sol or gel in water at room temperature. Suitable gelling agents for inclusion in the coating of this embodiment (if such are contained in the coating) include the above-described gelling agents which form solutions in water at room temperatures. In addition, it has been found that agar, after it has been dissolved in boiling water and deposited as a coating, is a material which is "cold-water-reconstitutable".

A preferred coating mixture is prepared by mixing the following ingredients:

| | |
|---|---|
| Proteose Peptone No. 3 | 50 grams |
| Porcine Peptone | 14 grams |
| Yeast Extract | 6 grams |
| Sodium chloride | 10 grams |
| MOPS acid | 3.2 grams |
| MOPS sodium salt | 5.2 grams |
| Phenol red | 1.0 grams |
| Bile Salts No. 3 | 2.0 grams |
| 5-Bromo-4-Chloro-3-Indoxyl-β-D-galactopyranoside | 0.8 grams |
| Guar | 13 grams |
| Deionized Water | 1 Liter |

It will be appreciated by a person of ordinary skill in the art that the above mixture includes at least two selective agents (e.g., sodium chloride and bile salts No. 3). It further will be appreciated by a person of ordinary skill in the art that the above mixture includes at least two components (e.g., phenol red and 5-Bromo-4-Chloro-3-Indoxyl-β-D-galactopyranoside) that can function as a differential indicator or a portion of a differential indicator system. For example, phenol red can be used in a formulation with a metabolizable compound (e.g., 2-deoxy-D-ribose or urea) to form a differential indicator system to indicate the presence of a microorganism such as a *Salmonella* microorganism, for example. *Salmonella* microorganisms can ferment 2-deoxy-D-ribose to acid byproducts, thereby producing an acid zone that can be visually detected in the presence of a pH indicator. *Salmonella* microorganisms further can react with 5-Bromo-4-Chloro-3-Indoxyl-α-D-galactopyranoside to form black-colored colonies. Non-*Salmonella* microorganisms (e.g., coliform microorganisms) can react with 5-Bromo-4-Chloro-3-Indoxyl-β-D-galactopyranoside, forming blue-green-colored colonies. Surprisingly, even though the aforementioned chromogenic enzyme substrates both comprise the same chromophor (5-Bromo-4-Chloro-3-Indoxyl-), in the inventive article of the present disclosure, they are hydrolyzed by the microorganisms to produce visually-distinct colored products. The indicator systems may be incorporated into the culture device in an adhesive layer, a powder layer, and/or a dry, rehydratable coating.

In addition to the selective ingredients listed in the above mixture, the coating mixture can further comprise a highly-selective combination of antibiotics that permit the growth of *Salmonella* microorganisms, while substantially preventing the growth of a variety of other (e.g., "nontarget") microorganisms. A nonlimiting example of such a combination includes a mixture of Cefsulodin sodium salt (about 12 mg/L), Nalidixic Acid sodium salt (about 4 mg/L), Streptomycin sulfate salt (about 4 mg/L), and methicillin sodium salt (about 45 mg/L), Referring back to FIG. 1, the cover sheet 124 includes a spacer element 118 applied to the surface of cover sheet 124 that faces the substrate 112. The spacer element 118 includes a circular hole 122 cut through the center to expose the dry, rehydratable coating 120 on the cover sheet 124. The walls of the hole 122 provide a well of predetermined size and shape to confine the medium following hydration. Spacer element 118 should be thick enough to form a well of the desired volume, e.g., 1, 2 or 3 milliliter. Closed cell polyethylene foam or polystyrene foam are preferred materials for spacer element 118, but any material which is hydrophobic (non-wetting), inert to microorganisms, and capable of withstanding sterilization may be used.

Also shown in FIG. 1 is a perforation 126 traversing the cover sheet 124. The perforation 126 facilitates opening the culture device 110 and, in some embodiments, can hold the culture device 110 open, as shown in FIG. 2.

Figure 2:
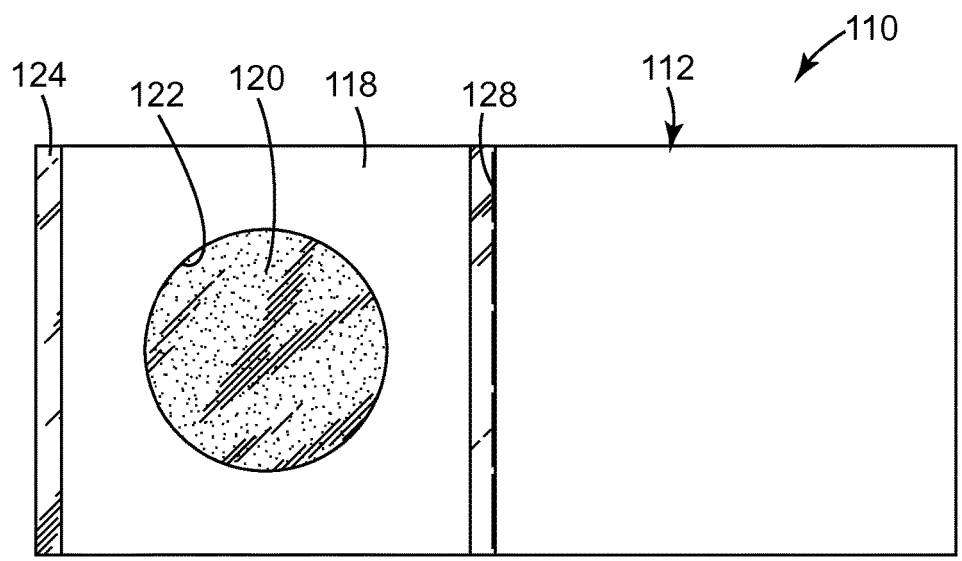
FIG. 2 is a top view of the culture device of FIG. 1 showing the culture device in an "open" position for inoculating the device.

FIG. 2 shows a top view of an open culture device 110 of the present disclosure. Shown in FIG. 2 are the substrate 112, cover sheet 124, spacer element 118, hole 122, and perforation 126. In this position, a liquid sample (not shown) can be placed onto the substrate 112 or in the well formed by the spacer element 118 to inoculate the plate.

A thin film culture device of the present disclosure can be used to test a sample for the presence of a *Salmonella* microorganism. Sample materials include sample materials that are suspected of containing a *Salmonella* microorganism. The sample material may be a liquid, a solid, a solid suspended or dispersed in a liquid, a hydrogel. In any of the embodiments, the sample may comprise microorganisms and/or materials (e.g., food, beverages) that have been subjected to one or more sample preparation techniques including but not limited to concentration (e.g., by filtration, precipitation, agglomeration, centrifugation, absorption, and/or adsorption), enrichment (e.g., selective growth enrichment), and purification (e.g., chromatographic purification).

In one embodiment, a predefined volume of liquid sample can be contacted with the coating on the cover sheet and the powder on the substrate to hydrate the culture device and form an inoculated culture device. In an alternative embodiment, water-reconstitutable coatings of the culture device may be hydrated with an aqueous liquid (e.g., sterile water) and the sample can be applied (e.g., by pipette, swab, loop), optionally using the streak-plate technique, to the hydrated culture device. Preferably, a coating in the culture device comprises a first indicator system (e.g., 2-deoxy-D-ribose and a pH indicator such as phenol red), a nondifferential indicator system (e.g., TTC), and a second indicator system (e.g., 5-Bromo-4-Chloro-3-Indoxyl-β-D-galactopyranoside, "X-gal"). Optionally, the culture device may comprise an inducer for a microbial activity associated with one or more of the indicator systems such as isopropyl-β-D-thiogalactoside, an inducer of β-galactosidase enzyme activity. Another differential indicator system used to indicate the presence of a *Salmonella* microorganism comprises urea and a pH indicator such as phenol red, for example.

After inoculating the culture device, the culture device can be incubated for a period of time to facilitate the growth of *Salmonella* microorganisms. A person of ordinary skill in the art will recognize the optimum temperature to facilitate the growth of *Salmonella*. The culture device can be incubated for about 0.5 to about 48 hours, preferably about 0.5 to about 24 hours, more preferably, about 0.5 hours to about 6 hours.

After the incubation period, the inoculated culture medium can be observed for an indication of a possible presence of a *Salmonella* microorganism. One indication is the appearance of red colonies due to the formation of formazan dye from TTC. Even further, an acid zone surrounding a red colony indicates the bacteria in the colony fermented 2-deoxy-D-ribose to acid byproducts, a reaction that can indicate the colony comprises *Salmonella* microorganisms. If the colony has a blue-green-colored zone associated with a reaction with X-gal, this indicates that the colony is probably not a *Salmonella* microorganism.

The presence of red colonies surrounded by an acid zone (e.g., a yellow zone when the pH indicator is phenol red) suggests the presence of a *Salmonella* microorganism in the culture device. This presumptive result can be further supported by contacting another differential indicator (e.g., 5-Bromo-4-Chloro-3-Indoxyl-α-D-galactopyranoside) with the colony. In some embodiments, this can be done by opening the plate and applying a solution of 5-Bromo-4-Chloro-3-Indoxyl-α-D-galactopyranoside to the growth medium. Alternatively, this can be done by opening the plate and applying a dry, rehydratable article comprising a coating that includes 5-Bromo-4-Chloro-3-Indoxyl-α-D-galactopyranoside. The article can be made as described in U.S. Pat. No. 6,022,682, which is incorporated by reference in its entirety. The 5-Bromo-4-Chloro-3-Indoxyl-α-D-galactopyranoside is contacted with the growth zone of the culture device for a period of time such as, for example about 30 minutes to about 360 minutes. Optionally, the contact can occur at an elevated temperature (e.g., 37° C.).

After contacting the 5-Bromo-4-Chloro-3-Indoxyl-α-D-galactopyranoside with the growth medium, the culture device can be observed for a very dark (e.g., nearly black) color associated with the colonies. Any red colony associated with an acid zone and a very dark (e.g., nearly black) color from the hydrolysis of 5-Bromo-4-Chloro-3-Indoxyl-α-D-galactopyranoside is very likely a *Salmonella* microorganism.

EMBODIMENTS

Embodiment 1 is a culture device for detecting a target microorganism, comprising:
a selective growth medium that includes nutrients to facilitate the growth of the target microorganism and a plurality of selective agents that includes Cefsulodin, Nalidixic Acid, Streptomycin, Methicillin, and bile salts;
a first differential indicator system; and
a gelling agent.

Embodiment 2 is the culture device of embodiment 1, further comprising a nondifferential indicator system to indicate the presence of the target microorganism.

Embodiment 3 is the culture device of any one of the preceding embodiments, wherein the first differential indicator system comprises a pH indicator.

Embodiment 4 is the culture device of any one of the preceding embodiments, further comprising a second differential indicator system to indicate the presence of a nontarget microorganism.

Embodiment 5 is the culture device of embodiment 4, wherein the second differential indicator comprises a chromogenic β-galactosidase enzyme substrate.

Embodiment 6 is the culture device of embodiment 4 or embodiment 5, further comprising an inducer of microbial β-galactosidase enzyme activity.

Embodiment 7 is the culture device of any one of the preceding embodiments, wherein the selective growth medium comprises a dry, rehydratable selective growth medium, wherein the gelling agent comprises a dry, cold water-soluble gelling agent.

Embodiment 8 is the culture device of embodiment 7, wherein the culture device comprises a thin film culture device.

Embodiment 9 is a system for the detecting a *Salmonella* microorganism, comprising:
a culture device comprising a nutrient medium that is highly selective for *Salmonella* microorganisms and at least two differential indicator systems, wherein a first differential indicator system is a positive indicator of the *Salmonella* microorganism, wherein a second differential indicator system is a negative indicator of the *Salmonella* microorganism; and a detection article comprising a third differential indicator system, wherein the third differential indicator system is a positive indicator of the *Salmonella* microorganism.

Embodiment 10 is the system of embodiment 9, wherein each of the second and third differential indicator systems comprises a chromogenic enzyme substrate, wherein each chromogenic enzyme substrate comprises a carbohydrate component and a chromophore.

Embodiment 11 is the system of embodiment 10, wherein each of the second and third differential indicator systems comprises the same chromophore.

Embodiment 12 is the system of any one of embodiments 9 through 11, wherein the second differential indicator system comprises a chromogenic indicator of β-galactosidase enzyme activity.

Embodiment 13 is the system of any one of embodiments 9 through 11, wherein the third differential indicator system comprises a chromogenic indicator of α-galactosidase enzyme activity.

Embodiment 14 is a method of detecting *Salmonella* microorganisms, comprising:
providing a liquid sample, the culture device of any one of embodiments 1 through 8, and a third differential indicator system;
contacting a predefined volume of the sample, in the culture device, with the selective growth medium; the first indicator system; the nondifferential indicator system, if present; the second indicator system, if present; and the gelling agent to form an inoculated culture device;
incubating the inoculated culture device for a first period of time;
observing the inoculated growth medium to detect an indication of a possible presence in the sample of the target microorganism;
when there is an indication of the possible presence of the target microorganism, contacting the third differential with the hydrated growth medium; and
observing the third differential indicator system in the hydrated growth medium for an indication of the presence of the target microorganism.

Embodiment 15 is a method of detecting *Salmonella* microorganisms, comprising:
providing a sample, the culture device of embodiment 8, and a third differential indicator system;
in the culture device, contacting a predefined volume of a *Salmonella*-free aqueous liquid with the selective growth medium; the first differential indicator system; the nondifferential indicator system, if present; the second differential indicator system, if present; and the gelling agent to form a hydrated growth medium;
inoculating the hydrated growth medium with the sample to form an inoculated culture device;
incubating the inoculated culture device for a first period of time;
observing the hydrated growth medium to detect an indication of a possible presence in the sample of the target microorganism;
when there is an indication of the possible presence of the target microorganism, contacting the third differential with the hydrated growth medium; and
observing the third differential indicator system in the hydrated growth medium for an indication of the presence of the target microorganism.

Embodiment 16 is the method of embodiment 14 or embodiment 15, wherein detecting an indication of the possible presence of the target microorganism further comprises observing a colony that reacts with the nondifferential indicator system and the first differential indicator system but does not react with the second differential indicator system.

Embodiment 17 is the method of any one of embodiments 14 through 16 wherein, after contacting the second component with the hydrated growth medium, the method further comprises incubating the culture device for a second period of time.

Embodiment 18 is the method of any one of embodiments 14 through 17, wherein incubating the inoculated culture device for a first period of time comprises incubating the inoculated culture device for about 0.5 hours to about 24 hours.

Embodiment 19 is the method of embodiment 18, wherein incubating the inoculated culture device for a first period of time comprises incubating the inoculated culture device for about 0.5 hours to about 6 hours.

Embodiment 20 is the method of any one of embodiments 14 through 19, wherein incubating the inoculated culture device for a second period of time comprises incubating the inoculated culture device for about 30 minutes to about 360 minutes.

EXAMPLES

The present invention should not be considered limited to the particular examples described below, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. Unless otherwise stated, all percentages and parts are by weight. Materials, unless otherwise stated are commercially available from Alpha Biosciences, Baltimore, Md.

Materials

Example 1

Preparation of a Salmonella Detection Article

A base member for a thin film culture plate was prepared according to Example 4 of U.S. Pat. No. 5,409,838 except that the adhesive was coated onto a waterproof polyethylene coated paper having a 0.5 inch square grid lines on it. A powder composition was prepared by have mixing 2 parts by weight of 2-deoxy-D-ribose (2DR) and 98 parts of guar gum (M150 guar MEYPROGAT gum, Meyhall Chemical AG). A small of amount (less than 0.5%) of silica (CAB-O-SIL silica, Cabot Corp., Boston Mass.) was added as needed for processing. The powder mixture was then sprinkled onto the adhesive coated paper, and tilted and tapped lightly to remove the excess powder.

A broth mixture was prepared by adding the materials listed in Table 1 to 1 liter of deionized water in a container, and mixed according to the method described in Example 1 of U.S. Pat. No. 6,022,682.

TABLE 1

| Material | Amount - Grams |
| --- | --- |
| Proteose peptone No. 3 | 50 |
| Porcine peptone | 14 |
| Yeast extract | 6 |

TABLE 1-continued

| Material | Amount - Grams |
| --- | --- |
| Sodium chloride | 10 |
| MOPS, acid (3-[N-morpholino]-propanesulfonic acid) | 3.2 |
| MOPS, sodium salt | 5.2 |
| Phenol red, sodium salt | 1.0 |
| Bile salts No. 3 | 2.0 |
| *5-Bromo-4-Chloro-3-Indoxyl-beta-D-galactopyranoside | 0.8 |
| Guar | 13 |

*from Biosynth AG, Switzerland

A selective agent mixture was prepared by adding 12 mg of Cefsulodin sodium salt (Research Products International, Chicago, Ill.), 4 mg of Nalidixic Acid sodium salt (Sigma Aldrich, St. Louis Mo.), 4 mg of Streptomycin sulfate salt (Sigma), 45 mg of methicillin sodium salt (Sigma), 0.4 mg of Isopropyl-B-D-galactopyranoside (Sigma), and 2 g of urea (EMD), to 20 ml of sterile deionized water, and swirled in a glass flask until completely dissolved. The broth was cooled to about 40° C. and the selective mixture was added with vigorous mixing.

A cover film and thin film culture plates were prepared as described in Example VI U.S. Pat. No. 6,022,682 except the selective broth was coated onto the corona-treated side of a 2.9 mil thick polyester film for the cover film. The plates measured approximately 7.6 cm by 10.2 cm with a 5 cm diameter circle cut from the foam to provide a well in about the center of the plate.

Example 2

Method of Detecting Salmonella Microorganisms

A pure culture of Salmonella bacteria (3M Culture Designation FSDCC SAL140 that was isolated from a meat mixture) was inoculated into Buffered Peptone Water (Merck, Darmstadt, Germany) and incubated overnight at 37° C. The resulting broth had a concentration of approximately $1\times10^9$ colony forming units/ml (cfu/ml). The broth was diluted in sterile Buffered Peptone Water to a final concentration of approximately $1\times10^6$ cfu/ml.

The thin film culture plate of Example 1 was prepared for streaking by adding 1.5 mL of Butterfield's Buffer to about the middle of the position of the well on the powder coating. The cover film was closed and the gel was allowed to hydrate for about one hour. When the cover film was opened, the broth coating had transferred to the gel surface. A 10 microliter loop of the final concentration was streaked onto the broth surface on the gel. The cover was closed and the plate was incubated overnight at 37 C. Plates were analyzed for colony counts. Red dots indicating colonies were apparent.

Example 3

Using an Indicator Article to Detect Salmonella Microorganisms

A disk described in Examples 1 and 2 of U.S. Patent Application No. 61/428,722, which is incorporated herein by reference in its entirety, is placed on top of the colonies and the disk is incubated at 37° C. The disk is examined for growth after 3, 4 and 5 hours.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified. Various modifications may be made without departing from the spirit and scope of the invention. These and other embodiments are within the scope of the following claims.

The invention claimed is:

1. A method of distinguishing a colony of non-*Salmonella* microorganisms from a colony of *Salmonella* microorganisms, the method comprising
    forming an inoculated culture device by combining in a dry film culture device comprising a film substrate and a cover sheet:
        a dry selective growth medium that includes a gelling agent; nutrients to facilitate the growth of *Salmonella* microorganisms; and a plurality of selective agents that includes Nalidixic Acid, Streptomycin, and bile salts;
        a first differential indicator system comprising 2-deoxy-D-ribose and a pH indicator;
        a second differential indicator system comprising a chromogenic β-galactosidase enzyme substrate;
        a third differential indicator system comprising urea; and
        a predefined volume of a liquid sample;
        wherein the dry selective growth medium is adhered to the substrate;
    incubating the inoculated culture device for a period of time;
    observing the inoculated culture device to detect a bacterial colony surrounded by an acid zone; and
    observing the bacterial colony to detect a blue-green-colored zone proximate the colony, wherein the blue-green-colored zone is associated with a reaction involving the β-galactosidase enzyme substrates;
    determining whether the bacterial colony is a *Salmonella* microorganism or a non-*Salmonella* microorganism;
        wherein observing a bacterial colony that is surrounded by the acid zone and that does not have a blue-green-colored zone proximate the colony indicates the bacterial colony is a colony of *Salmonella* microorganisms;
        wherein observing a bacterial colony that is surrounded by the acid zone and that does have a blue-green-colored zone proximate the colony indicates the bacterial colony is a colony of a non-*Salmonella* microorganisms.

2. The method of claim 1, wherein forming the inoculated culture device comprises:
    depositing the predefined volume of the liquid sample into a culture device that comprises the selective growth medium, the first differential indicator system, and the second differential indicator system;
    incubating the inoculated culture device for a first period of time;
    observing the inoculated culture device to detect a bacterial colony surrounded by an acid zone;
    when a bacterial colony surrounded by the acid zone is observed, contacting the selective growth medium with a detection article comprising the third differential indicator system;
    incubating the inoculated culture device for a second period of time; and
    observing the inoculated culture device to detect a bacterial colony reacting with the urea.

3. The method of claim 2, wherein incubating the inoculated culture device for a first period of time comprises incubating the inoculated culture device for about 0.5 hours to about 24 hours.

4. The method of claim 3, wherein incubating the inoculated culture device for a first period of time comprises incubating the inoculated culture device for about 0.5 hours to about 6 hours.

5. The method of claim 2, wherein incubating the inoculated culture device for a second period of time comprises incubating the inoculated culture device for about 30 minutes to about 360 minutes.

* * * * *

UNITED STATES PATENT AND TRADEMARK OFFICE
CERTIFICATE OF CORRECTION

PATENT NO. : 9,593,361 B2  
APPLICATION NO. : 14/118258  
DATED : March 14, 2017  
INVENTOR(S) : Patrick Mach et al.

Page 1 of 1

It is certified that error appears in the above-identified patent and that said Letters Patent is hereby corrected as shown below:

In the Specification

Column 4
Line 18, delete "-Enterobactericeae:" and insert -- -Enterobacteriaceae: --, therefor.
Line 29, delete "and or" and insert -- and/or --, therefor.

Column 7
Line 52, delete "mg/L)," and insert -- mg/L). --, therefor.

In the Claims

Column 14
Line 2, in Claim 1, delete "substrates;" and insert -- substrate; --, therefor.

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*